United States Patent [19]

Larson et al.

[11] Patent Number: 5,230,626
[45] Date of Patent: Jul. 27, 1993

[54] ABSORBENT DENTAL DEVICE

[76] Inventors: William A. Larson, 78-6954 Walua Rd., Kailua-Kona, Hi. 96740; Dale P. Wilterink, 40581 Corte Lucia, Murietta, Calif. 92562

[21] Appl. No.: 818,623

[22] Filed: Jan. 10, 1992

[51] Int. Cl.$^5$ .................. A61C 5/14; A61C 17/06; A61C 17/14
[52] U.S. Cl. ........................ 433/136; 433/91
[58] Field of Search ........... 433/91, 93, 94, 96, 433/136; 604/11, 12

[56] References Cited

U.S. PATENT DOCUMENTS

| | | | |
|---|---|---|---|
| 1,742,080 | 12/1929 | Jones | 433/136 |
| 2,644,234 | 7/1953 | Scott | 433/136 |
| 3,091,859 | 6/1963 | Baughan | 433/94 |
| 4,233,025 | 11/1980 | Larson et al. | 433/136 |
| 4,792,326 | 12/1988 | Tews | 604/11 |
| 5,071,347 | 12/1991 | McGuire | 433/97 |
| 5,094,616 | 3/1992 | Levenson | 433/93 |

FOREIGN PATENT DOCUMENTS 3122834 12/1982 Fed. Rep. of Germany ...... 433/136

Primary Examiner—Gene Mancene
Assistant Examiner—Cherichetti Cindy A.
Attorney, Agent, or Firm—Spensley Horn Jubas & Lubitz

[57] ABSTRACT

An absorbent dental device has an inner core roll of absorbent material adjustably telescoped within a hollow cylindrical outer roll of absorbent material. The adjustable positioning of the inner core roll within the hollow outer roll permits adjustably sizing of the device, while the pliant material of the rolls facilitates shaping of the device. The device may be used separately as a fluid and debris absorbing device within the patient's mouth during a dental procedure. The device may also be used as an aspirator cover to prevent damage of the mouth tissues and promote patient comfort while at the same time providing the aspirator with an extension of desired size and shape.

8 Claims, 2 Drawing Sheets

ABSORBENT DENTAL DEVICE

BACKGROUND OF THE INVENTION

1. Field of the Invention

The present invention relates to devices for absorbing oral fluids during dental procedures, and more particularly to absorbent devices of cotton or similar construction which are placed in a patient's mouth separately or in association with an aspirator.

2. History of the Prior Art

It is well known in the field of dentistry to provide means for removing fluids such as saliva as well as debris from the mouth of a patient during various procedures. For example, it is common to use strips or rolls of cotton or other absorbent material or sponges, which are placed in the patient's mouth during the procedures. Alternatively, or in addition to the cotton rolls and sponges, aspirators are used.

Where aspirators are used, one end of the aspirator is inserted in the mouth and the other end is connected to a source of suction. This permits continuous evacuation of fluids and debris from the patient's mouth. The aspirator typically sits on the floor of the patient's mouth, so that the suction is applied directly to the tissues of the inside of the mouth and is not always gentle. This is often uncomfortable for the patient. To minimize such discomfort, a chairside assistant may be necessary in order to handle the aspirator and to move it from place to place to ensure continuous absorption of the oral fluids without irritation to the sensitive tissues of the mouth.

It is known to provide a soft absorbent device as a cover for the aspirator to minimize irritation to the inside of the mouth. An example of such a device is shown in U.S. Pat. No. 4,233,025 of William A. Larson and Dale P. Wilterink, which patent issued Nov. 11, 1980 and is entitled "Hollow Cotton Roll". The Larson, et al. patent describes a hollow cotton roll which is placed over the tip of the aspirator. As a result, the suction of the aspirator is made more gentle, patient comfort is increased, the suction roar is muffled, and chairside assistance is typically not needed to handle the aspirator. The hollow roll can be placed in an autoclave or otherwise subjected to high temperatures in connection with the sterilization procedures that are increasingly being required.

While the hollow cotton roll described in the Larson, et al. patent works well for many applications, there may be situations where an improved absorbent device would be advantageous. In particular, it would be advantageous to provide absorbent devices of adjustable size and which can be shaped to conform to specific areas of the patient's mouth. Thus, the strips or rolls of cotton or other absorbent material or sponges commonly placed in the patient's mouth to absorb fluids and debris are typically of fixed size and are difficult to shape or contour to fit specific areas of the mouth. Moreover, aspirator covers such as the hollow cotton roll shown in the Larson, et al. patent are typically of fixed size and do not lend themselves to adjustable sizing or shaping.

It would therefore be advantageous to provide an absorbent dental device having an adjustable size and capable of shaping so as to assume various different desired configurations. This would provide considerable versatility in terms of use of such devices in different areas of a patient's mouth to absorb fluids. It would also be advantageous to provide an absorbent dental device capable of use as an aspirator cover while at the same time having an adjustable size and an adjustable configuration so that a shaped extension as well as a protective cover for the aspirator is provided.

SUMMARY OF THE INVENTION

Briefly stated, the present invention provides an absorbent device for dental and similar procedures, including surgery, requiring fluid absorption. Devices in accordance with the invention have an adjustable size and can be shaped so as to conform to a variety of different fluid absorbing applications. Such devices are also capable of serving as an aspirator cover in order to protect the sensitive tissues on the inside of the patient's mouth, in addition to being adjustable in both size and configuration so as to form a shaped extension of the aspirator. The devices can be sterilized in an autoclave without damage thereto.

Absorbent dental devices in accordance with the invention include an inner member of absorbent material adjustably telescoped within a hollow outer member which is also made of absorbent material. The telescoped positioning of the inner member within the outer member permits varying the length of the absorbent device. In addition, the inner and outer members of the device are of pliable as well as absorbent construction to permit shaping of the device in order to conform to specific applications therefore.

In a preferred embodiment of an absorbent dental device according to the invention, the inner member comprises an inner core roll of absorbent construction telescoped within a hollow cylindrical outer roll of absorbent construction. The outer roll is constructed so as to be normally biased into an oblong or oval cross-sectional shape to secure the inner core roll at a desired position therein. However, by depressing the edges of the outer roll, the inner core roll is free to slide so that it can be adjustably repositioned within the outer roll. In this manner the position of the inner core roll within the outer roll can be adjusted to provide the device with a desired length. At the same time, the pliable nature of both the inner core roll and the outer roll, which are made essentially of cotton or similar absorbent material, enables the device to be curved, flattened, or otherwise shaped. The absorbent dental device may also be used as an aspirator cover, in which event the inner core roll is moved partly out of the outer roll to permit receipt of the end of the aspirator within the hollow interior of the outer roll. The inner core roll may be moved still further to a desired position within the outer roll, and the device may be bent and otherwise reconfigured to provide a shaped extension for the aspirator.

BRIEF DESCRIPTION OF THE DRAWINGS

A better understanding of the invention may be had by reference to the following description in conjunction with the accompanying drawings, in which.

DETAILED DESCRIPTION

Figure 1:
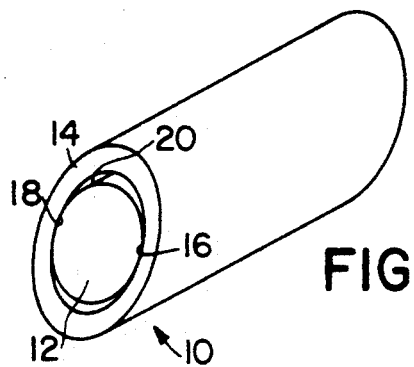
FIG. 1 is a perspective view of an absorbent dental device in accordance with the invention.

FIG. 1 illustrates a preferred embodiment of an absorbent dental device 10 in accordance with the invention. The device 10 is comprised of an inner core roll 12 of absorbent material and a hollow outer roll 14 which is also of absorbent material. The inner roll 12 is in the shape of a solid cylinder. The outer roll 14 is of hollow, generally cylindrical configuration but biased in the construction thereof so as to normally assume an oblong or other non-circular cross-sectional shape. Consequently, the outer roll 14 contacts the inner core roll 12 at opposite sides 16 and 18 of an inner surface 20 thereof.

Figure 2:
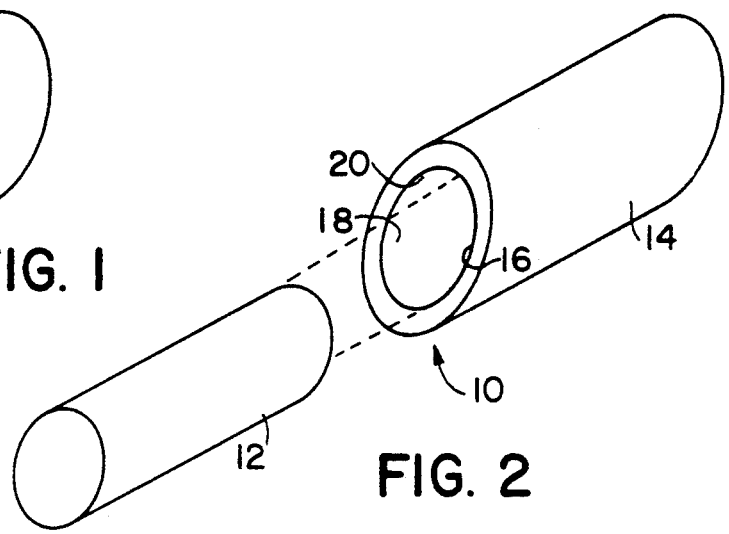
FIG. 2 is an exploded perspective view of the device of FIG. 1.

FIG. 2 is an exploded view of the device 10 of FIG. 1, showing the solid cylindrical shape of the inner roll 12 and the hollow, generally cylindrical shape of the outer roll 14. The inner roll 12 has the same length as the outer roll 14, which is 1.5 inches in the present example, but which can be any length desired. The inner surface 20 of the outer roll 14 defines a hollow interior of the outer roll 14 which is slightly larger than the inner roll 12. The inner roll 12 has an outer diameter of approximately $\frac{1}{4}$ inch in the present example. Because the outer roll 14 normally assumes an oblong cross-sectional shape, the opposite sides 16 and 18 of the inner surface 20 are biased against the inner roll 12 to hold the roll 12 at a desired position within the outer roll 14.

The adjustable telescoping of the inner core roll 12 within the hollow outer roll 14 in the device 10 provides the device 10 with an adjustable length. In addition, both the inner roll 12 and the outer roll 14 are made of pliable material so that the device 10 may be shaped as well as sized for various oral applications, as described hereafter. The inner roll 12 and the outer roll 14 may be constructed basically of cotton or other absorbent material. The outer roll 14, for example, can be constructed in a manner similar to the hollow cotton roll of the previously referred to Larson, et al. patent. As described in detail in that patent, the hollow cotton roll thereof includes a layer of an open-mesh fabric, such as gauze stiffened with starch, defining an inner wall of the roll. A layer of an absorbent material, such as cotton or a synthetic fabric, surrounds the open-mesh fabric. An outer layer of braided yarn surrounds the absorbent material to retain the same. The Larson, et al. patent also describes in detail methods and apparatus for making such a hollow cotton roll.

Alternative forms of construction of the hollow outer roll 14 are possible. For example, the layer of absorbent material surrounding the open-mesh fabric can comprise non-woven cotton, or synthetic felt. Also, the hollow outer roll 14 can be constructed without a woven, open-mesh inner wall.

The inner roll 12 may be constructed in a fashion similar to the outer roll 14. Thus, the inner roll 12 may comprise a mass of absorbent material, such as cotton or a synthetic fabric, surrounded by a layer of braided yarn. Alternatively, other forms of construction are possible.

The absorbent dental device 10 may be manufactured using a conventional braiding machine which has been modified so as to simultaneously bond the multiple yarns or filaments to the absorbent filler material to prevent fraying when the resulting roll is cut to form the individual dental devices 10. A braiding machine with a plurality of bobbin carriers as shown in the previously referred to U.S. Pat. No. 4,233,025 of Larson et al. can be used for this purpose. With such a braiding machine, the inner roll 12 is first formed by drawing cotton or other absorbent material through a round former or die of approximately $\frac{1}{4}$ inch inside diameter while simultaneously braid-covering and bonding to the absorbent material. In this manner, the inner roll 12 of approximately $\frac{1}{4}$ inch outside diameter is formed. In a second operation, the formed inner roll 12 is drawn up through a center guide in the braiding machine, where it is wrapped with an open mesh fabric inner liner, then absorbent material formed by a special oval-profile former or die, and simultaneously braid-covered and bonded to the absorbent material. The maximum width or diameter of the oval-shaped device is approximately 9/16 inch and the minimum thickness or diameter is approximately $\frac{3}{8}$ inch.

The inner roll 12 may be manufactured with a continuous colored yarn embedded and glued within the absorbent material. The yarn end may be grasped with tweezers to move the inner roll 12 within the outer roll 14 instead of pushing the inner roll 12 through with a blunt object or with the tip of an aspirator.

Alternative methods of manufacture can be used. For example, formation of the outer roll 14 can be accomplished by pulling the fabric of absorbent covering material through a machine, folding one edge over the other, and bonding by adhesive or heat sealing.

Typically, the inner roll 12 and the outer roll 14 are formed in a generally continuous length which must be cut at regular intervals to form the absorbent dental devices 10. Such continuous formation may be cut at $1\frac{1}{2}$ inch intervals or at any lengths desired using a conventional knife wheel machine, an oscillating straight knife machine, or an automatic pull-through guillotine knife cutting machine.

Figure 3:
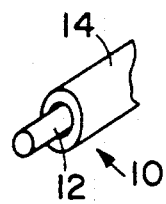
FIG. 3 is a perspective view of the device of FIG. 1 with the inner core roll extending outside of the outer roll by a relatively small amount.

As previously noted, the device 10 can be sized and shaped to assume a variety of different desired configurations for use as a fluid absorbing device within the patient's mouth. As shown in FIG. 3, one end of the inner roll 12 has been moved outside of the outer roll 14 by a relatively small amount so as to extend the length of the device 10 by relatively a small amount. At the same time, the pliable construction of the inner and outer rolls 12 and 14 permits bending, flattening and other shaping of the device 10 as desired.

Figure 4:
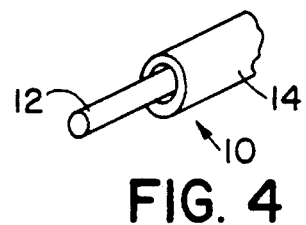
FIG. 4 is a perspective view similar to FIG. 3 but with the inner core roll extending outside of the outer roll by a greater amount.

The inner roll 12 can be moved to the outside of the outer roll 14 by an even greater amount to provide the device 10 with a greater length, as shown in FIG. 4. Again, the device 10 can also be shaped by bending, flattening and other manipulation to assume a desired configuration.

The adjustable size and the ability to shape the device 10 enables the device 10 to be used in a variety of different locations within the patient's mouth as an absorbent device. Thus, adjusting the device 10 to a relatively long length provides an absorbent roll ideally suited for the buccal areas of the mouth. The device 10 may be formed into a horse shoe shape for bucclingual applications on the mandibular.

Where desired, the inner and outer rolls 12 and 14 may be completely separated and used separately as absorbent devices within the mouth. The hollow outer roll 14, by itself, provides a very soft and pliable absorbent device. The inner core roll 12 is useful in the anterior area of the mouth, where the space for such devices is relatively small, as well as with children where the mouth cavities are smaller.

Figure 5:
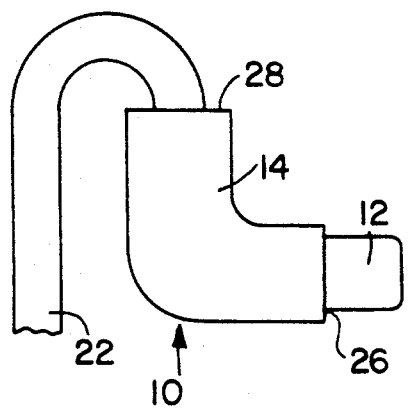
FIG. 5 is a side view of the device of FIG. 1 mounted on the end of a conventional aspirator.
Figure 6:
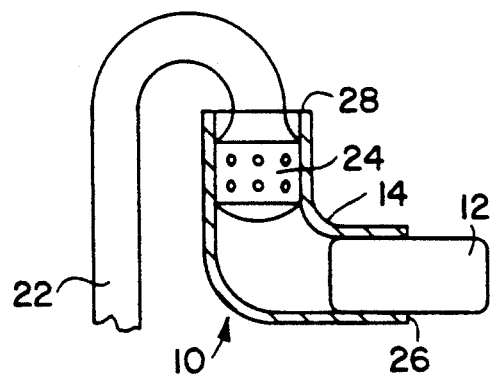
FIG. 6 is a view similar to FIG. 5 but with the outer roll of the device of FIG. 1 shown in section.

In addition to comprising an expandable absorbent roll of adjustable size which may be sized and shaped as desired for various absorbent applications within the mouth, the device 10 may also be used as an aspirator cover. FIG. 5 shows a conventional aspirator 22 with the device 10 mounted on an end thereof. FIG. 6 is a view similar to FIG. 5 but with the outer roll 14 of the device 10 being shown in section, so that the interior details of the device 10 are clear. As shown in FIG. 6, the aspirator 22 terminates in a ventilated end 24 through which the source of suction coupled to the aspirator 22 communicates with the patient's mouth to withdraw fluids. Normally, the end 24 rests directly on the tissues at the inside of the patient's mouth. However, in the example of FIGS. 5 and 6, the device 10 is used as a cover for the aspirator 22 in addition to providing an absorbent aspirator extension of desired shape. The inner roll 12 is positioned so as to extend outside of a lower open end 26 of the hollow outer roll 14. An opposite upper end 28 of the hollow outer roll 14 extends over and receives the end 24 of the aspirator 22. The hollow outer roll 14 is curved through a generally right-angle bend so as to form an elbow-like extension from the end 24 of the aspirator 22, with the position of the inner roll within the outer roll 14 determining the length of such extension.

The device 10 mounted on the aspirator 22 in the arrangement of FIGS. 5 and 6 protects the patient's mouth from tissue irritation and damage that might otherwise result if the end 24 of the aspirator 22 were placed in direct contact with such tissues. At the same time, fluids may be drawn into the end 24 of the aspirator 22 through the inner core roll 12 and the hollow outer roll 14, which are both porous in nature. Solid debris such as filling material tends to become embedded in or to cling to the device 10, and is removed from the mouth upon withdrawal of the aspirator 22. This frequently makes it unnecessary that a separate suctioning device be used to clean the mouth. The elbow-shaped configuration of the device 10 shown in FIGS. 5 and 6 provides the aspirator 22 with n extension of desired size and shape to provide fluid absorption in desired areas of the mouth as well as facilitating desired placement of the aspirator 22 within the mouth.

Figure 7:
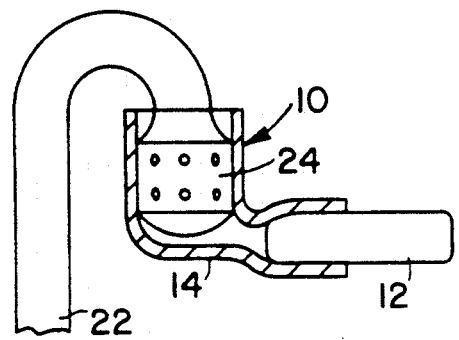
FIG. 7 is a side view of the device of FIG. 1 mounted on an aspirator with the outer roll of the device shown in section, and with the device being adjusted in size and shape to form a desired extension for the aspirator.
Figure 8:
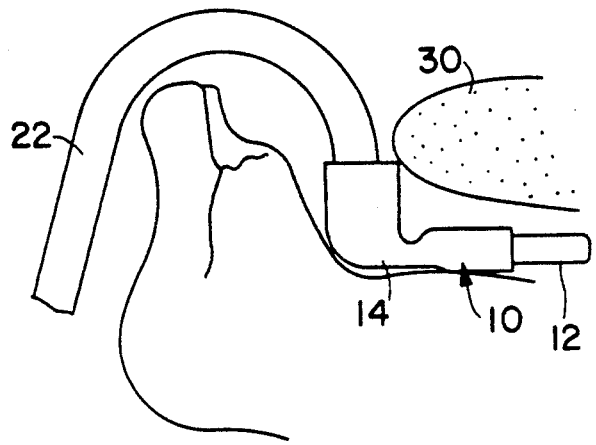
FIG. 8 is a view similar to FIG. 7 and showing the manner in which the arrangement of FIG. 7 may be placed within a patient's mouth so that the extension formed by the device extends under the tongue.

The manner in which the device 10 may be shaped as well as sized to assume specific desired configurations is shown in FIGS. 7 and 8. In FIGS. 7 and 8 the device 10 is curved through a generally right-angle bend, much in the manner of FIGS. 5 and 6. However, an intermediate portion of the outer roll 14 is compressed in a manner so that the outer roll 14 undergoes a rather abrupt lateral extension from the end 24 of the aspirator 22. At the same time the inner roll 12 is telescopically positioned within the hollow outer roll 14 to provide the extension formed by the device 10 with a desired size as well as shape. As shown in FIG. 8, such configuration is ideally suited for placement of the aspirator 22 over the lower teeth and onto the floor of the mouth. The device 10, in addition to covering the end 24 of the aspirator 22 and protecting the mouth tissues therefrom, also extends underneath the tongue 30 so as to absorb fluids therefrom in addition to aspirating the floor of the mouth.

Figure 9:
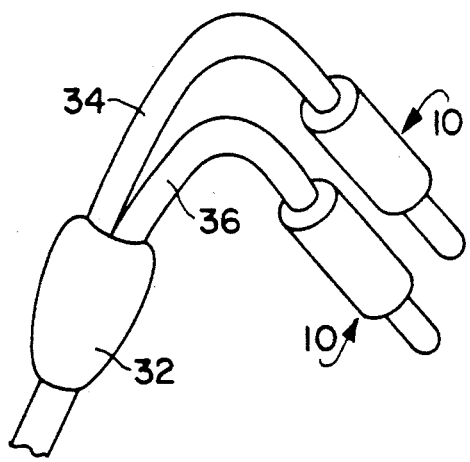
FIG. 9 is a perspective view of a dual aspirator with a pair of the devices of FIG. 1 mounted thereon.

The device 10 may be used as a cover for other aspirator configurations as well. Thus, s shown in FIG. 9, a dual aspirator configuration 32 has two different aspirators 34 and 36. Each of the aspirators 34 and 36 is provided with a different one of the absorbent dental devices 10.

A desirable feature of the absorbent dental device 10 is that it can be subjected to high temperatures for sterilization purposes, both when used alone and when used as an aspirator cover. This is desirable in today's disease-conscious environment, where it is frequently a requirement that devices to be placed in a patient's mouth must first be sterilized in an autoclave. The materials used in the construction of the device 10 withstands such high temperatures without damage or destruction.

While use of the device 10 as an aspirator cover is advantageous for practically all aspirator applications in which patient comfort and tissue irritation or damage is a concern, it is particularly advantageous in those situations where there is little or no opportunity to adjust the aspirator once placed in the patient's mouth. An example of this is where a rubber dam is placed over portions of the patient's face and mouth to isolate a particular tooth being worked on. In such instances, the aspirator is placed in the mouth before application of the dam, making it difficult or impossible to adjust the aspirator while the dam is in place. In such instances, use of the device 10 as a cover for the aspirator protects the inside of the mouth from the aspirator while at the same time enhancing the comfort of the patient. In still other instances, a single placement of the device 10 is all that is necessary. This virtually eliminates the need for the rubber dam. With the device 10 used as a cover for the aspirator, aspiration is virtually noiseless.

For certain dental procedures such as pulp testing and to control bleeding, it is common practice to place in the patient's mouth one or more absorbent devices which have ben soaked in water and frozen. Conventional absorbent rolls are commonly treated in this manner. Unfortunately, such rolls tend to defrost rather quickly, necessitating frequent replacement during a dental procedure.

Absorbent dental devices 10 in accordance with the invention can be provided with a core of ice which remains frozen for a relatively long period of time. The inner roll 12 is pushed out of the outer roll 14, and the outer roll is then soaked with water and frozen. This forms a core of ice on the inside of the outer roll 14. One or more of the outer rolls 14 as so formed with the core of ice are then placed in the patient's mouth for pulp testing and to control bleeding. The inner core of ice which is disposed within the outer roll 14 melts relatively slowly, so that the rolls do not require frequent replacement. The inner rolls 12 can also be soaked and frozen and used in such procedures.

While the invention has been particularly shown and described with reference to a preferred embodiment thereof, it will be understood by those skilled in the art that various changes in form and details may be made therein without departing from the spirit and scope of the invention.

What is claimed is:

1. An absorbent dental device comprising the combination of:
   a hollow outer member of absorbent material; and
   an inner member of absorbent material slidable relative to and adjustably telescoped within the hollow outer member;
   the hollow outer member normally assuming a non-circular cross-sectional shape so as to engage and compress the inner member therein.

2. An absorbent dental device comprising the combination of:
   a hollow outer member of absorbent material; and
   an inner member of absorbent material slidable relative to and adjustably telescoped within the hollow outer member;
   the hollow outer member being of generally cylindrical shape and having a given length and the inner member being of solid cylindrical shape and having a length substantially equal to the given length, the outer member normally assuming an oblong cross-sectional shape.

3. An absorbent dental device comprising the combination of:
   a hollow outer member of absorbent material; and
   an inner member of absorbent material slidable relative to and adjustably telescoped within the hollow outer member;
   the outer member and the inner member being both made primarily of cotton.

4. An absorbent dental device comprising the combination of:
   a hollow outer member of absorbent material; and
   an inner member of absorbent material adjustably telescoped within the hollow outer member;
   the outer member comprising a layer of open mesh fabric defining an inner wall, a layer of absorbent material surrounding the fabric layer, and a layer of braided yarn surrounding the absorbent material; and
   the inner member comprising a solid member of absorbent material and a layer of braided yarn surrounding the absorbent material.

5. An absorbent dental device for use with an aspirator, comprising:
   an outer member of soft, absorbent material having a hollow interior; and
   an inner member of absorbent material slidable relative to and telescoped within part but not all of the hollow interior of the outer member so that a remaining portion of the hollow interior can receive an end of an aspirator therein.

6. An absorbent dental device according to claim 5, wherein the outer member is of pliable construction and the inner member is of pliable construction to permit shaping of the device.

7. An absorbent dental device according to claim 5, wherein the outer member is of generally cylindrical configuration and has a given length and the inner member is of cylindrical configuration and has a length substantially equal to the given length, the inner member being disposed partly within and partly outside of the hollow interior of the outer member.

8. An absorbent dental device according to claim 7, wherein the outer member normally assumes a non-circular cross-sectional shape so as to compress and hold the inner member in a desired position therein.

* * * * *